United States Patent [19]

Satterstrom

[11] Patent Number: Plant 6,712

[45] Date of Patent: Apr. 4, 1989

[54] PLUM TREE, VIKING PRIDE

[76] Inventor: Joseph W. Satterstrom, 12299 E. Magnolia, Kingsburg, Calif. 93631

[21] Appl. No.: 114,155

[22] Filed: Oct. 29, 1987

[51] Int. Cl.[4] ..... A01H 5/03
[52] U.S. Cl. ..... Plt./38
[58] Field of Search ..... Plt./38

*Primary Examiner*—Robert E. Bagwill
*Attorney, Agent, or Firm*—Worrel & Worrel

[57] ABSTRACT

A new and distinct variety of plum tree which is denominated varietally as "Viking Pride" and which is somewhat similar to the Durado Plum Tree (U.S. Plant Pat. No. 3,925) with which it is most closely related, the subject variety characterized by producing fruit which have a deep red skin color and a yellow flesh color, and which is ripe for commercial harvesting approximately June 13 in the San Joaquin Valley of central California.

1 Drawing Sheet

BACKGROUND OF THE NEW VARIETY

The present invention relates to a plum tree denominated varietally as "Viking Pride", and more particularly to such a plum tree which bears dark red fruit which ripen approximately ten days later than the "Durado" Plum Tree (U.S. Plant Pat. No. 3,925), from which it was derived as a bud sprout, and approximately one week prior to the "Black Beaut" Plum Tree (U.S. Plant Pat. No. 3,615), which matures in approximately the same season. The Viking Pride Plum Tree is further characterized as to novelty by producing fruit which has a delicate flavor and a flesh texture which is substantially firmer than the fruit produced by the Durado Plum Tree. In addition the new variety displays noteworthy holding characteristics uncommon to the varieties with which it is most closely similar.

The Durado Plum Tree is well known as a vigorous producer of early maturing fruit, the fruit of the Durado Plum Tree characterized by a red to dark red skin color and a green-amber flesh; the fruit further being freestone by nature, and having excellent eating qualities.

It has long been recognized that it would be desirable to have a plum tree that somewhat remotely resembles the Durado Plum Tree but which bears fruit which are ripe for commercial harvesting later in the season, whereby the commercial demand for such a plum can be effectively satisfied over a greater period of time.

ORIGIN AND ASEXUAL REPRODUCTION OF THE NEW VARIETY

The new and distinct variety of plum tree hereof was discovered by the applicant in 1982 as a bud sprout on a Durado Plum Tree, the subject tree growing in a commercial orchard owned by the applicant and located on Magnolia Avenue in Kingsburg, Calif. The bud sprout was noted at that time to have desirable characteristics. Scion wood of the new variety was subsequently taken by the applicant in February, 1985 and grafted onto Nemagard root stock seedlings. It has been subsequently determined that this first asexual propagation resulted in progeny being produced that possess the same distinctive characteristics as the original bud sprout.

SUMMARY OF THE NEW VARIETY

The Viking Pride variety of plum tree is characterized as to novelty by producing fruit which are mature for commercial harvesting approximately ten days later than the Durado Plum Tree (U.S. Plant Pat. No. 3,925) and about one week prior to the Black Beaut Plum Tree (U.S. Plant Pat. No. 3,617), both plum trees maturing in approximately the same season. The fruit of the subject plum tree is further characterized as to novelty by producing fruit which have a dark red skin color, a yellow colored flesh and a delicate flavor.

BRIEF DESCRIPTION OF THE DRAWINGS

The accompanying drawing is a color photograph of four mature fruit of the subject variety, one of which has been divided in the suture plane to show the flesh characteristics, together with a twig bearing typical leaves showing the dorsal and ventral coloration thereof, and two stones, all of the subject variety.

DETAILED DESCRIPTION

Referring more specifically to the pomological details of this new and distinct variety of plum tree, the following has been observed under the ecological conditions prevailing at the orchard of the inventor which is located on Magnolia Avenue near Kingsburg, Calif. All major color code designations are by reference to the Dictionary of Color by Maerz and Paul, Second Edition, 1950. However, common color names are also employed occasionally.

TREE

Size:
- *Generally.*—Medium to large depending upon pruning practices.

Vigor: Vigorous.
Figure: Upright; open; vase-formed; and tender.
Productivity: Variable, medium productive through productive.
Regularity of bearing: Regular.
Trunk:
- *Thickness.*—Medium.
- *Texture of bark.*—Shaggy.

Branches:
- *Thickness.*—Variable, medium to slender.
- *Texture of bark.*—Average.
- *Color.*—A dull gray.

Lenticels:
- *Numbers.*—Medium.
- *Size.*—Small.

LEAVES

Size:

*Generally.*—Medium to large.

*Length.*—Variable, 8.0 through 10.5 mm., average length, approximately 9.3 mm.

*Width.*—Variable, 3.6 through 4.9 cm., average width 4.37 cm.

*Form.*—Lanceolate; acuminate to acutely pointed.

*Thickness.*—Average to thin.

*Texture.*—Smooth.

*Marginal form.*—Finely serrate.

*Petiole — Length.*—Short.

*Petiole — Thickness.*—Slender.

*Glands 13 Numbers.*—Variable, two through four, generally, however just two.

*Glands — Position.*—Opposite.

*Glands — Form.*—Globose.

*Glands — Color.*—Green.

*Glands — Position.*—At the base of the blade.

*Stipules.*—Not present.

*Leaf color — dorsal surface.*—Pale green, Plate 24, J-10 (pg. 71).

*Leaf color — ventral surface.*—Green, Plate 22, D-3, (Pg. 67).

Flowers: The flower buds and flowers of the subject variety are not distinctive.

FRUIT

Maturity when described: Ripe for commercial harvesting and shipment approximately June 13, the variety matures uniformly thereby permitting harvesting during a single picking.

*First pick* 1987.—June 8, 1987.

*Last pick* 1987.—June 13, 1987.

Size: Variable, medium to large.

*Uniformity.*—Uniform; unsymmetrical and compressed. The fruit is rounded, and has a flat area or slight depression at the pistil end.

*Axial diameter.*—Variable, 3.8 to 4.9 cm. (average diametral dimension 4.2 cm).

*Diameter transverse in the suture plane.*—Variable, 4.9 to 6.0 cm. (average diametral dimension 5.4 cm.).

*Diameter in the cheek plane.*—Variable, 5.2 to 6.2 cm. (average diametral dimension 5.7 cm.).

Suture: An inconspicuous shallow line which extends from the base, but discontinues at the apex; the suture displays a slight depression beyond the pistil point.

Ventral surface: Rounded slightly; lips are unequal.

Cavity:

*Generally.*—Flaring, and circular.

*Depth.*—Approximately 7.2 mm.

*Breadth.*—Approximately 8 mm.

*Markings.*—No distinctive markings are evident.

Base:

*Form.*—Truncate.

Apex:

*Form.*—Truncate, and slightly depressed.

Skin:

*Thickness.*—Average.

*Texture.*—Medium to tough.

*Tenacious to flesh.*—Yes.

*Color.*—Dark red, 48 L3 or L4 (Pg. 119).

*Down.*—Variable, wanting, occasionally none may be present.

Flesh:

*Color.*—Yellow, Plate 4, B-6 (Pg. 45).

*Surface of pit cavity.*—Color — yellow with slight reddish spots.

*Amygdalin.*—Scant.

*Juice production.*—Rich, juicy.

*Texture.*—Firm.

*Fibers.*—Few and fine.

*Ripening.*—Even.

*Flavor.*—Mild to subacid.

*Aroma.*—Wanting.

*Eating quality.*—Good.

Stone:

*Generally.*—Adheres to the flesh over the entire surface.

*Fibers.*—Short.

*Size.*—Generally — small.

*Average length.*—Approximately 15.3 mm.

*Average breadth.*—Approximately 16.84 mm.

*Average thickness.*—Approximately 9.65 mm.

*Form.*—Rounded, and flat.

*Hilum.*—Narrow.

*Apex.*—Rounded.

*Sides.*—Equal and flattened; the stone is irregularly furrowed at the ventral edge and near the base.

*Pitting.*—Absent, or occasionally very shallow.

*Ridges.*—Rounded.

*Pits.*—Elongated and thin.

*Ventral edge.*—Thin.

*Dorsal edge.*—Narrow.

*Ridges.*—Interrupted.

*Color of stone.*—Brown, Plate 12, A-10, (pg. 47).

*Tendency to split.*—No splitting is evident.

*Resistance to insects and disease.*—No special susceptibilities were noted.

*Shipping quality.*—Good — The new variety appears to hold better than the fruit produced by the Durado Plum Tree (U.S. Plant Pat. No. 3,925).

Although the new variety of plum tree possesses the described characteristics as a result of the growing conditions prevailing in Fresno County, Calif., in the central part of the San Joaquin Valley, it is to be understood that variations in the usual magnitude and characteristics incident to growing conditions, fertilization, pruning and pest control are to be expected.

Having thus described and illustrated my new variety of Plum Tree, what is claimed as new and desired to be secured by Letters Patent is:

1. A new and distinct variety of plum tree substantially as illustrated and described which is somewhat similar to the Durado Plum Tree (U.S. Plant Pat. No. 3,925) with which it is most closely related but from which it is distinguished as to novelty by bearing fruit which are large, uniform and a dark red color, the fruit ripening for commercial harvesting approximately ten days after the Durado Plum Tree and approximately one week prior to the Black Beaut Plum Tree (U.S. Plant Pat. No. 3,617) which matures at approximately the same time of the season.

* * * * *

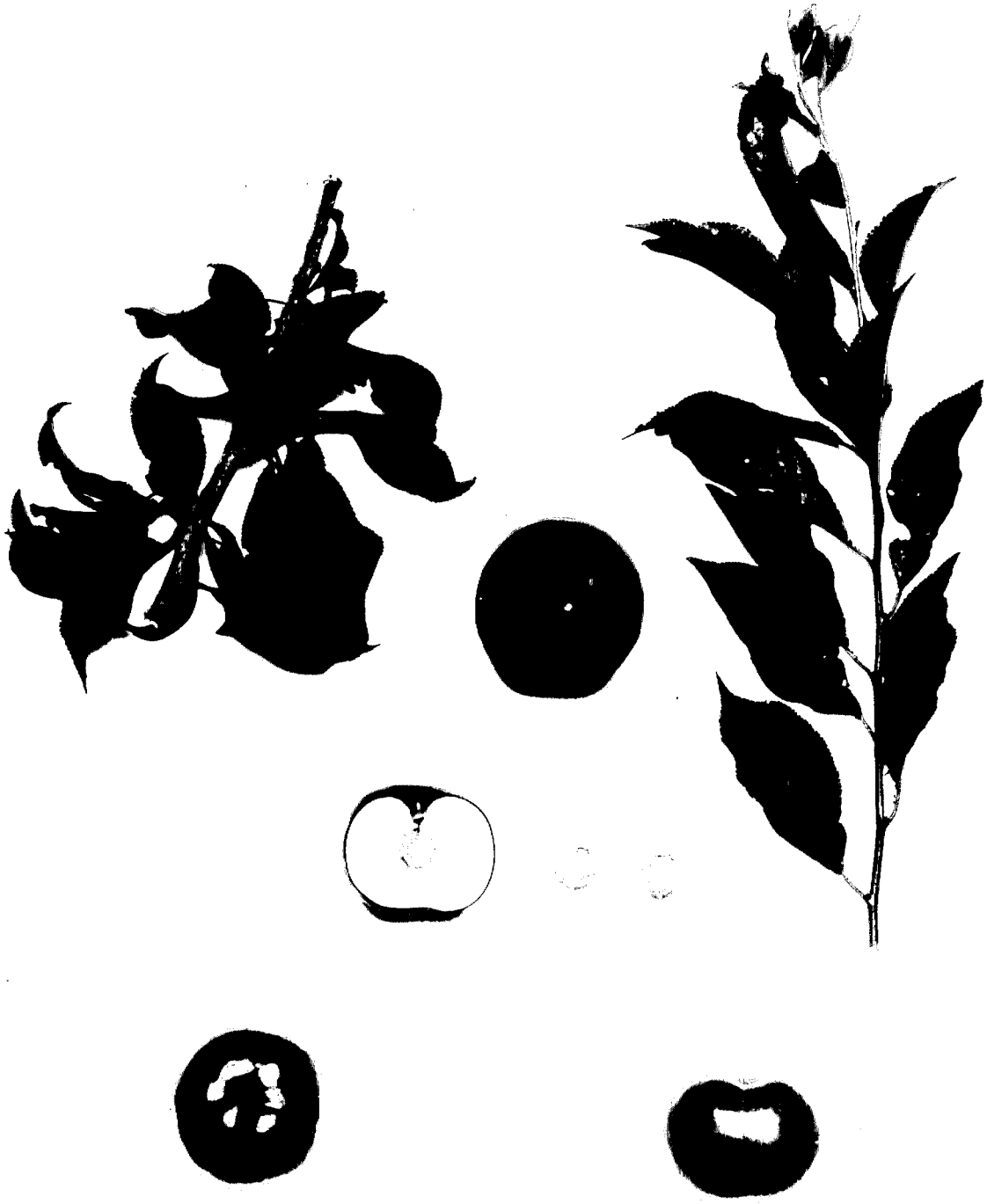

UNITED STATES PATENT AND TRADEMARK OFFICE

CERTIFICATE OF CORRECTION

PATENT NO. : PP 6,712

DATED : April 4, 1989

INVENTOR(S) : Joseph W. Satterstrom

It is certified that error appears in the above-identified patent and that said Letters Patent is hereby corrected as shown below:

Column 3, Line 15

Delete "13"

Insert -

Signed and Sealed this

Fourteenth Day of November, 1989

*Attest:*

JEFFREY M. SAMUELS

*Attesting Officer*

*Acting Commissioner of Patents and Trademarks*